(12) United States Patent
Thornton

(10) Patent No.: US 7,677,889 B2
(45) Date of Patent: Mar. 16, 2010

(54) DEVICE AND METHOD FOR FORMING A CUSTOM ORAL APPLIANCE

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 177 days.

(21) Appl. No.: 11/830,467

(22) Filed: Jul. 30, 2007

(65) Prior Publication Data

US 2008/0032256 A1 Feb. 7, 2008

Related U.S. Application Data

(60) Provisional application No. 60/821,620, filed on Aug. 7, 2006.

(51) Int. Cl.
*A61C 19/04* (2006.01)
(52) U.S. Cl. ............................................. 433/68; 433/6
(58) Field of Classification Search ............ 433/54–71, 433/6; 128/859–862, 848
See application file for complete search history.

(56) References Cited

U.S. PATENT DOCUMENTS

| 690,663 | A | 1/1902 | Pratt |
|---|---|---|---|
| 746,869 | A | 12/1903 | Moulton |
| 774,446 | A | 11/1904 | Moulton |
| 885,196 | A | 4/1908 | Steil |
| 893,213 | A | 7/1908 | Whiteway |
| 955,562 | A | 4/1910 | Thomas |
| 996,783 | A | 7/1911 | Moreau |
| 1,076,534 | A | 10/1913 | Wallen |
| 1,146,264 | A | 7/1915 | Kelly |
| 1,483,694 | A | 2/1924 | Stukey |
| 1,592,345 | A | 7/1926 | Drager |
| 1,649,664 | A | 11/1927 | Carter |

(Continued)

FOREIGN PATENT DOCUMENTS

DE       2 320 501       11/1974

(Continued)

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

(Continued)

*Primary Examiner*—Cris L Rodriguez
*Assistant Examiner*—Matthew M Nelson
(74) *Attorney, Agent, or Firm*—Baker Botts L.L.P.

(57) ABSTRACT

In one embodiment, a method includes: accessing a bite register with a post, upper and lower dental models, and a fixture having upper and lower plates and a clamp; coupling the register post to the fixture, such that the register post has a first orientation; coupling the upper and lower models to the register; coupling the upper and lower models to the upper and lower plates; uncoupling the register; coupling an appliance post to the fixture, such that the appliance post has a second orientation the same as the first orientation; and forming a custom oral appliance coupled to the appliance post and maintaining the second orientation of the appliance post. In one embodiment, a device is configured to couple to an articulator and to position and retain a bite register post. The device includes a lower member, first and second couplers, an upper member, and an adjustor.

21 Claims, 8 Drawing Sheets

U.S. PATENT DOCUMENTS

| | | | |
|---|---|---|---|
| 1,674,336 A | 6/1928 | King | |
| 1,675,202 A | 6/1928 | Warne | |
| 1,679,748 A | 8/1928 | Stratton | |
| 2,171,695 A | 9/1939 | Harper | 32/19 |
| 2,178,128 A | 10/1939 | Waite | 128/136 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,712,160 A | 7/1955 | Sterczek | 18/55.05 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Comiello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,360,860 A | 1/1968 | Roland | 32/17 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,690,004 A | 9/1972 | Frush | 32/17 |
| 3,854,208 A | 12/1974 | Arant | 32/19 |
| 3,864,832 A | 2/1975 | Carlson | 32/40 R |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,289,127 A | 9/1981 | Nelson | 128/207.14 |
| 4,304,227 A | 12/1981 | Samelson | 128/136 |
| 4,376,628 A | 3/1983 | Aardse | 433/80 |
| 4,382,783 A | 5/1983 | Rosenberg | 433/19 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,454,090 A | 6/1984 | Saumell | 264/154 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,715,368 A | 12/1987 | George | 128/136 |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,605 A | 8/1989 | Levy | 128/203.11 |
| 4,862,903 A | 9/1989 | Campbell | 128/861 |
| 4,892,478 A | 1/1990 | Tateosian et al. | 433/6 |
| 4,901,737 A | 2/1990 | Toone | 128/848 |
| 4,932,867 A | 6/1990 | Ueno | 433/69 |
| 4,955,393 A | 9/1990 | Adell | 128/859 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,064,371 A | 11/1991 | Smeltzer | 433/37 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,213,498 A | 5/1993 | Pelerin | 433/37 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,409,017 A | 4/1995 | Lowe | 128/848 |
| 5,415,544 A | 5/1995 | Oxman et al. | 433/48 |
| 5,427,117 A | 6/1995 | Thornton | 128/848 |
| 5,503,552 A | 4/1996 | Diesso | 433/37 |
| 5,537,994 A | 7/1996 | Thornton | 128/204.18 |
| 5,551,872 A | 9/1996 | Mena | 433/37 |
| 5,562,449 A | 10/1996 | Jacobs et al. | 433/215 |
| 5,566,683 A | 10/1996 | Thornton | 128/848 |
| 5,582,517 A | 12/1996 | Adell | 433/6 |
| 5,678,567 A | 10/1997 | Thornton et al. | 128/848 |
| 5,681,164 A | 10/1997 | Bass | 433/6 |
| 5,718,244 A | 2/1998 | Thornton | 128/864 |
| 5,720,302 A | 2/1998 | Belfer | 128/848 |
| 5,755,219 A | 5/1998 | Thornton | 128/201.18 |
| 5,807,100 A | 9/1998 | Thornton | 433/48 |
| 5,829,441 A | 11/1998 | Kidd et al. | 128/848 |
| 5,846,082 A | 12/1998 | Thornton | 433/215 |
| 5,891,372 A | 4/1999 | Bessett et al. | 264/46.5 |
| 5,954,048 A | 9/1999 | Thornton | 128/201.18 |
| 5,983,892 A | 11/1999 | Thornton | 128/201.26 |
| 6,083,442 A | 7/2000 | Gabilly | 264/163 |
| 6,109,265 A | 8/2000 | Frantz et al. | 128/848 |
| 6,155,262 A | 12/2000 | Thornton et al. | 128/859 |
| 6,209,542 B1 | 4/2001 | Thornton | 128/206.29 |
| 6,247,926 B1 | 6/2001 | Thornton | 433/48 |
| 6,305,376 B1 | 10/2001 | Thornton | 128/848 |
| 6,318,997 B1 | 11/2001 | Mayweather | 433/45 |
| 6,325,064 B1 | 12/2001 | Thornton | 128/204.18 |
| 6,374,824 B1 | 4/2002 | Thornton | 128/201.26 |
| 6,405,729 B1 | 6/2002 | Thornton | 128/848 |
| 6,464,924 B1 | 10/2002 | Thornton | 264/331.12 |
| 6,516,805 B1 | 2/2003 | Thornton | 128/848 |
| 6,571,798 B1 | 6/2003 | Thornton | 128/206.21 |
| 6,675,802 B1 | 1/2004 | Thornton | 128/206.29 |
| 6,845,774 B2 | 1/2005 | Gaskell | 128/848 |
| 6,877,513 B2 | 4/2005 | Scarberry et al. | 128/848 |
| 7,174,895 B2 | 2/2007 | Thornton et al. | 128/848 |

| | | | |
|---|---|---|---|
| 2004/0237965 A1 | 12/2004 | Bibi et al. | 128/206.29 |
| 2007/0125388 A1 | 6/2007 | Thornton et al. | 128/848 |
| 2007/0235037 A1 | 10/2007 | Thornton | 128/848 |
| 2008/0006273 A1 | 1/2008 | Thornton | 128/206.21 |
| 2008/0006274 A1 | 1/2008 | Thornton | 128/206.21 |
| 2008/0032256 A1 | 2/2008 | Thornton | 433/57 |

FOREIGN PATENT DOCUMENTS

| | | |
|---|---|---|
| DE | 29506512.5 | 7/1995 |
| EP | 0 312 368 A1 | 4/1989 |
| EP | 0 359 135 A1 | 3/1990 |
| GB | 1 569 129 | 6/1980 |
| GB | 2 072 567 A | 10/1981 |
| WO | WO 91/12777 | 9/1991 |
| WO | WO 98/26736 | 6/1998 |
| WO | WO 98/46177 | 10/1998 |

OTHER PUBLICATIONS

Photocopies of 2-piece dental device manufactured by Currie-Gibson Dental Lboratory, Inc., prior to Apr. 13, 1993, 5 pages.

Farrar, et al, *A Clinical Outline of Temporomandibular Joint Diagnosis and Treatment*, Normandie Study Group for TMJ Dysfunction, 3 pages, 1983.

Professional Positioners; *Dedicated to Excellence* brochure, 3 pages.

Great Lakes Orthodontics, Ltd.; *Nocturnal Airway Patency Applicance*; 2 pages.

Schmidt-Nowara, et al.; An American Sleep Disorders Association Review; *Oral Appliances for the Treatment of Snoring and Obstructive Sleep Apnea: A Review*; pp. 501-510, 1995.

George, Peter; *Treatment of Snoring and Obstructive Sleep Apnea with a Dental Device*; 5 pages, Jul.-Aug. 1993.

Database WOI, Section PQ, Week 9039, Derwent Publications, Ltd., London, GB; XP-002116355 Abstract—*Surgical Mouth Air Duct*; 1 page, Dec. 15, 1989.

PCT Notification of Transmittal of The International Search Report or the Declaration for International Application No. PCT/US97/08708, 4 pages, Aug. 12, 1997.

PCT Invitation to Pay Additional Fees for International Application No. PCT/US03/13705, 6 pages, Oct. 10, 2003.

PCT International Search Report and Written Opinion, International Application No. PCT/US06/26622, 11 pages, Feb. 21, 2007.

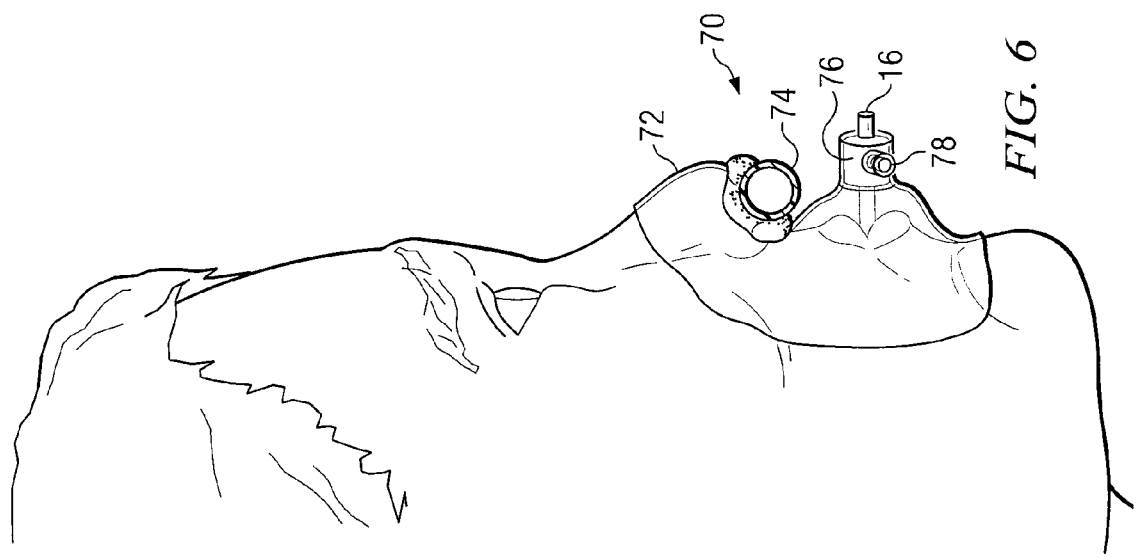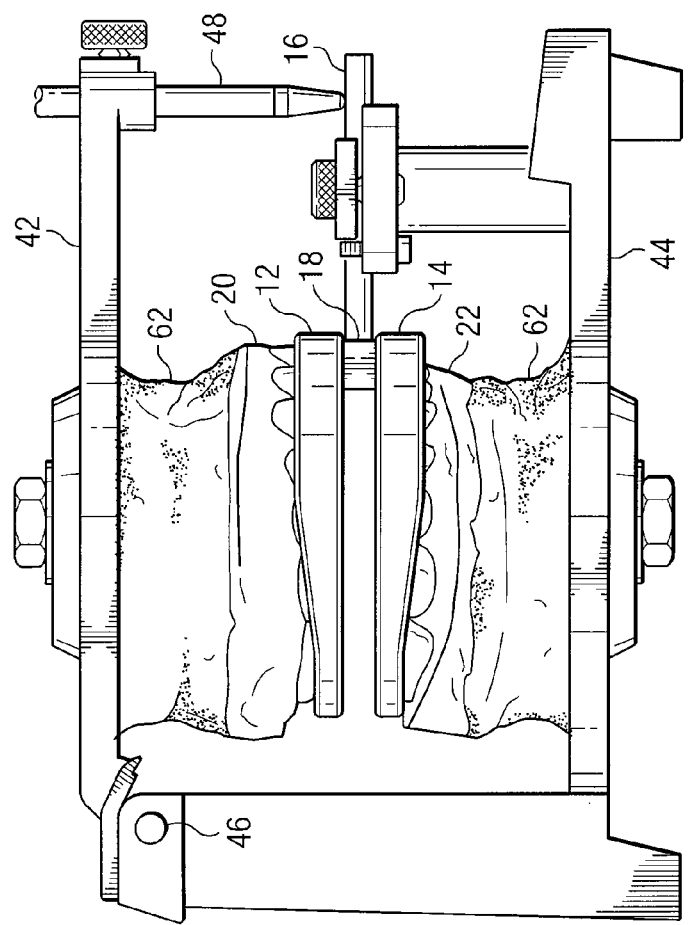

DEVICE AND METHOD FOR FORMING A CUSTOM ORAL APPLIANCE

RELATED APPLICATION

This application claims the benefit under 35 U.S.C. §119(e) of U.S. Provisional Application Ser. No. 60/821,620 filed Aug. 7, 2006.

TECHNICAL FIELD

This invention relates generally to oral appliances, and more particularly to a device and method for forming a custom oral appliance.

BACKGROUND

Many people experience breathing problems on a recurring basis, which often result in sleep disordered breathing (i.e., difficulty sleeping, snoring, or other more serious conditions such as obstructive sleep apnea). As technology advances, people with such breathing problems demand increased performance and comfort. Previous devices for improving a user's breathing have included oral appliances and clinical gas delivery devices. Examples of clinical gas delivery devices include face masks, nose masks, and nasal inserts that help deliver clinical gases to the user. These devices have been used with various positive air pressure systems to deliver air to the user's nose at a positive pressure to help force open the user's breathing passage and thereby improve the user's breathing. Examples of oral appliances include devices that are inserted into a user's mouth for adjustably extending the user's lower jaw forward. These devices open the breathing passageway more fully to allow easier breathing through the nose and mouth. Previous devices have also included combination systems including both oral appliances and clinical gas delivery devices. These combination systems have been used to obtain the benefits of both oral appliances and clinical gas delivery devices and/or to use the oral appliance to help secure the clinical gas delivery device in position. Previous fitting techniques for these combination systems have involved an iterative approach that has typically required the user to make multiple office visits to obtain satisfactory fit and performance.

Overview

According to one embodiment, a method for forming a custom oral appliance includes accessing a bite register for a particular user, the bite register comprising a post, an upper impression of at least some of the particular user's upper teeth, and a lower impression of at least some of the particular user's lower teeth; accessing an upper dental model of at least some of the particular user's upper teeth and a lower dental model of at least some of the particular user's lower teeth; and accessing a fixture comprising an upper plate, a lower plate, and a clamp and configured to repeatably position and secure a post. The method also includes coupling the bite register post to the fixture using the clamp of the fixture, such that the bite register post has a first orientation relative to the fixture; coupling the upper dental model and the lower dental model to the bite register, such that the upper dental model seats within the upper impression of the bite register and the lower dental model seats within the lower impression of the bite register; while the upper dental model is seated within the upper impression of the bite register and the bite register post is coupled to the fixture, coupling the upper dental model to the upper plate of the fixture; while the lower dental model is seated within the lower impression of the bite register and the bite register post is coupled to the fixture, coupling the lower dental model to the lower plate of the fixture; and while the upper dental model is coupled to the upper plate of the fixture and the lower dental model is coupled to the lower plate of the fixture, uncoupling the bite register from the upper dental model, the lower dental model, and the fixture. The method further includes coupling an oral appliance post to the fixture using the clamp of the fixture, such that the oral appliance post has a second orientation relative to the fixture, the second orientation of the oral appliance post being the same as the first orientation of the bite register post; and while the upper dental model, the lower dental model, and the oral appliance post are coupled to the fixture, forming a custom oral appliance that is custom-fitted to the upper dental model and the lower dental model, such that the custom oral appliance couples to the oral appliance post and maintains the second orientation of the oral appliance post.

According to another embodiment, a method for forming a custom oral appliance includes accessing a bite register for a particular user, the bite register comprising a post, an upper impression of at least some of the particular user's upper teeth, and a lower impression of at least some of the particular user's lower teeth; accessing an upper dental model of at least some of the particular user's upper teeth and a lower dental model of at least some of the particular user's lower teeth; accessing an upper arch custom-fitted to the upper dental model and configured to receive at least some of the particular user's upper teeth, a lower arch custom-fitted to the lower dental model and configured to receive at least some of the particular user's lower teeth, and a connector that couples the upper arch to the lower arch; and accessing a fixture comprising an upper plate, a lower plate, and a clamp and configured to repeatably position and secure a post. The method also includes coupling the bite register post to the fixture using the clamp of the fixture, such that the bite register post has a first orientation relative to the fixture; coupling the upper dental model and the lower dental model to the bite register, such that the upper dental model seats within the upper impression of the bite register and the lower dental model seats within the lower impression of the bite register; while the upper dental model is seated within the upper impression of the bite register and the bite register post is coupled to the fixture, coupling the upper dental model to the upper plate of the fixture; while the lower dental model is seated within the lower impression of the bite register and the bite register post is coupled to the fixture, coupling the lower dental model to the lower plate of the fixture; while the upper dental model is coupled to the upper plate of the fixture and the lower dental model is coupled to the lower plate of the fixture, uncoupling the bite register from the upper dental model, the lower dental model, and the fixture; and coupling an oral appliance post to the fixture using the clamp of the fixture, such that the oral appliance post has a second orientation relative to the fixture, the second orientation of the oral appliance post being the same as the first orientation of the bite register post. The method further includes positioning the upper arch relative to the upper dental model such that at least some of the teeth of the upper dental model seat within the upper arch; positioning the lower arch relative to the lower dental model such that at least some of the teeth of the lower dental model seat within the lower arch; and while the upper dental model, the lower dental model, and the oral appliance post are coupled to the fixture, and while at least some of the teeth of the upper dental model are received within the upper arch and at least some of the teeth of the lower dental model are received within the lower arch, coupling the oral appliance post to the connector coupling the upper arch to the lower arch to form a custom oral appliance that is custom-fitted to the upper dental model and the lower dental model and maintains the second orientation of the oral appliance post.

According to another embodiment, a method for forming a custom oral appliance includes accessing a bite register for a particular user, the bite register comprising an impression of at least some of the particular user's teeth; accessing a dental model of at least some of the particular user's teeth; and accessing a fixture comprising a plate and a clamp and configured to repeatably position and secure a post. The method also includes coupling the bite register post to the fixture using the clamp of the fixture, such that the bite register post has a first orientation relative to the fixture; coupling the dental model to the bite register, such that the dental model seats within the impression of the bite register; while the dental model is seated within the impression of the bite register and the bite register post is coupled to the fixture, coupling the dental model to the plate of the fixture; and while the dental model is coupled to the plate of the fixture, uncoupling the bite register from the dental model and the fixture. The method further includes coupling an oral appliance post to the fixture using the clamp of the fixture, such that the oral appliance post has a second orientation relative to the fixture, the second orientation of the oral appliance post being the same as the first orientation of the bite register post; and while the dental model and the oral appliance post are coupled to the fixture, forming a custom oral appliance that is custom-fitted to the dental model, such that the custom oral appliance couples to the oral appliance post and maintains the second orientation of the oral appliance post.

According to another embodiment, a device for use in forming a custom oral appliance includes a dental articulator and a clamp. The dental articulator is configured to substantially replicate jaw movement and comprises an upper plate configured to position and retain a first dental model, a lower plate configured to position and retain a second dental model, and a hinge configured to rotatably couple the upper plate to the lower plate. The clamp is coupled to the dental articulator and is configured to position and retain a post of a bite register.

According to another embodiment, a device for forming a custom oral appliance is configured to couple to a dental articulator and to position and retain a post of a bite register. The device includes a lower member, first and second couplers, an upper member, and a threaded adjustor. The lower member defines a channel to receive and position a post of a bite register. The first and second couplers couple to the lower member. The upper member includes an opening and a slot, the upper member configured to receive the first coupler through the opening and to engage the second coupler through the slot to position the upper member relative to the lower member. The threaded adjustor couples to the upper member and is configured to apply a force against the post of the bite register when the post of the bite register is received and positioned within the channel and the upper member is positioned relative to the lower member.

Certain embodiments may provide one or more technical advantages. For example, certain embodiments may provide a more accurate or efficient method of forming a custom oral appliance that does not require numerous iterations or repeated visits to the clinician's facilities. Certain embodiments may provide improved systems or methods to orient dental models to a dental fixture. Certain embodiments may provide for the formation of an oral appliance with a precisely oriented post that may be used to precisely and repeatably couple to one or more external devices, such as clinical gas delivery devices. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and certain of its advantages, reference is now made to the following description, taken in conjunction with the accompanying drawings, in which:

FIGS. 5A through 5E illustrate an example method of forming a custom oral appliance;

FIG. 6 illustrates an example mask for use with a custom oral appliance.

DESCRIPTION OF EXAMPLE EMBODIMENTS

Figure 1:
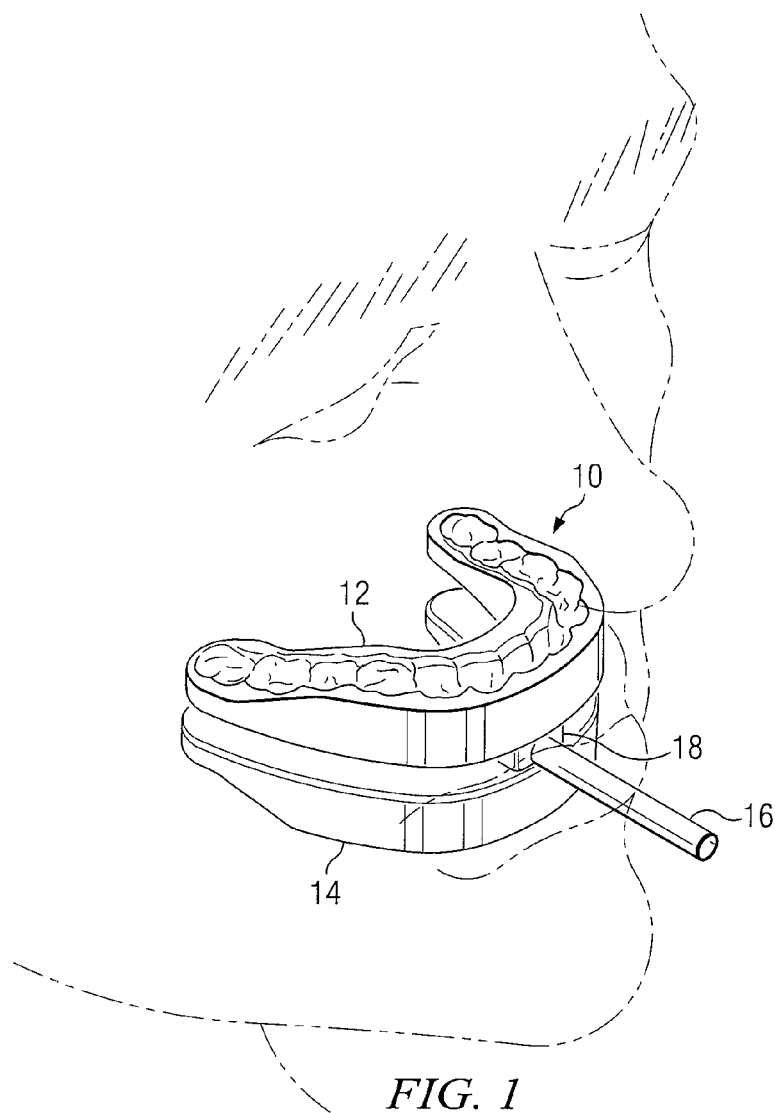
FIG. 1 illustrates an example custom oral appliance.

FIG. 1 illustrates an example custom oral appliance 10. Custom oral appliance 10 may be used to treat any of numerous medical or dental conditions. For example, custom oral appliance 10 may be used to treat sleep disordered breathing, such as snoring or obstructive sleep apnea. As shown in FIG. 1, oral appliance 10 includes an upper arch 12 configured to receive at least some of a particular user's upper teeth, and a lower arch 14 configured to receive at least some of the user's lower teeth. In certain embodiments, upper arch 12 and lower arch 14 may include custom molds of at least some of the user's upper and lower teeth, respectively, for improved fitting, performance, and comfort. Upper arch 12 and lower arch 14 may be formed from a deformable material suitable for dental uses. Examples of such deformable materials include methylmethacrylate, a polycarbonate resin thermoplastic such as LEXAN, ethylene-vinyl acetate copolymer resin such as ELVAX, and a polycaprolactone polymer such as TONE.

In operation, upper arch 12 may move freely with respect to lower arch 14, the movement of upper arch 12 and lower arch 14 may be limited in one or more directions relative to each other or upper arch 12 and lower arch 14 may be rigidly coupled together. In certain embodiments, upper arch 12 may be fully integral to lower arch 14. In alternative embodiments, upper arch 12 may be permanently or removably coupled to lower arch 14 using a connector 18. In a particular embodiment, connector 18 may be configured to adjustably couple upper arch 12 to lower arch 14. For example, connector 18 may be adjusted to pull lower arch 14 forward relative to upper arch 12 to facilitate improved breathing. Connector 18 may include a hook and an adjustment screw that may be adjusted to pull lower arch 14 forward. Connector 18 may define a precise vertical separation or range of vertical separations between upper arch 12 and lower arch 14 to precisely determine the opening of the user's lower jaw.

In certain embodiments, custom oral appliance 10 may include one or more structures that may be configured to couple custom oral appliance 10 to one or more other devices or structures. For example, as shown in FIG. 1, custom oral appliance 10 may include a post 16 configured to project out of the user's mouth when upper arch 12 and lower arch 14 are positioned within the user's mouth to receive at least some of the user's teeth. In certain embodiments, post 16 of custom oral appliance 10 may be configured to couple custom oral appliance 10 to another device positioned outside of the user's mouth. For example, post 16 may be configured to couple custom oral appliance 10 to a device that restricts or prevents a user from breathing through their mouth and/or to couple custom oral appliance to a clinical gas delivery device. An appropriate clinical gas delivery device for coupling to post 16 of custom oral appliance 10 may include, for example, a face mask, a nose mask, or nasal inserts that may help deliver clinical gas to the user from a clinical gas delivery system. A suitable clinical gas delivery system may be a Continuous Positive Air Pressure (CPAP) system, a Bilevel Positive Air Pressure (BiPAP) system, or other system configured to deliver air, oxygen, anesthetic, or other gases to the user. Further discussion of an example clinical gas delivery device for coupling to post 16 is provided below with reference to FIG. 6.

Although custom oral appliance 10 has been described according to certain embodiments as including upper arch 12, lower arch 14, post 16, and connector 18, in alternative embodiments custom oral appliance 10 may include only a single arch and post 16. In certain embodiments, custom oral appliance 10 may be formed using dental models, a bite register, and a fixture as discussed below with reference to FIGS. 2 through 4B.

Figure 2:
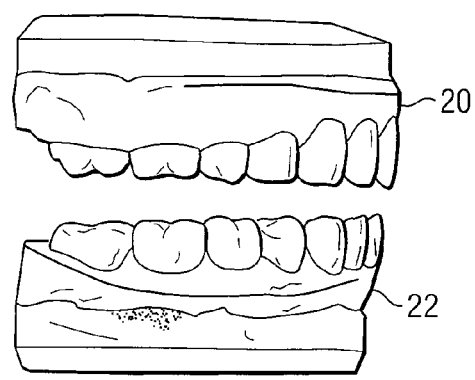
FIG. 2 illustrates example dental models for use in forming a custom oral appliance.

FIG. 2 illustrates example upper dental model 20 and lower dental model 22. Upper dental model 20 and lower dental model 22 represent physical replicas of at least some of a particular user's upper and lower teeth, respectively. Dental models 20 and 22 may be formed from plaster, stone, or any other appropriate material. In certain embodiments, dental models 20 and 22 may be formed through a casting process using physical impressions of the user's teeth. In alternative embodiments, dental models 20 and 22 may be formed using digital models and an appropriate rapid-prototyping process, such as stereolithography.

FIGS. 3A through 3D illustrate example embodiments of bite register 30. In the embodiments shown, bite register 30 includes bite plate 32 and post 34. Bite plate 32 is configured to be positioned between a user's upper and lower teeth to receive an impression of at least some of a particular user's teeth when the user bites down on bite plate 32. In the embodiment shown in FIGS. 3A and 3B, bite plate 32 includes a deformable material 36 that can deform to create an impression of at least some of the user's teeth. In certain embodiments, deformable material 36 may be made of wax or an appropriate polymer. In a particular embodiment, deformable material 36 may include BLU-MOUSSE, available from PARKELL, INC. in Edgewood, N.Y.

In certain embodiments, deformable material 36 is included on only one side of bite plate 32 to receive an impression of only the user's upper or lower teeth. In alternative embodiments, deformable material 36 is included on both sides of bite plate 32 to receive an impression of at least some of the user's upper and lower teeth to record their relative position or orientation.

Figure 3A:
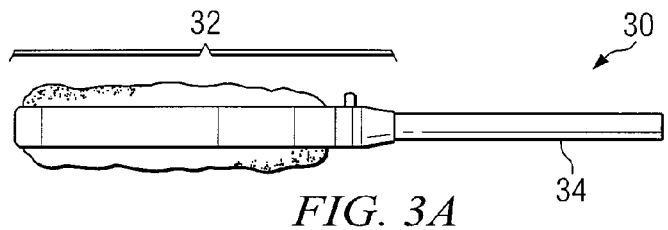
FIGS. 3A through 3D illustrate example bite registers for use in forming custom oral appliances.
Figure 3B:
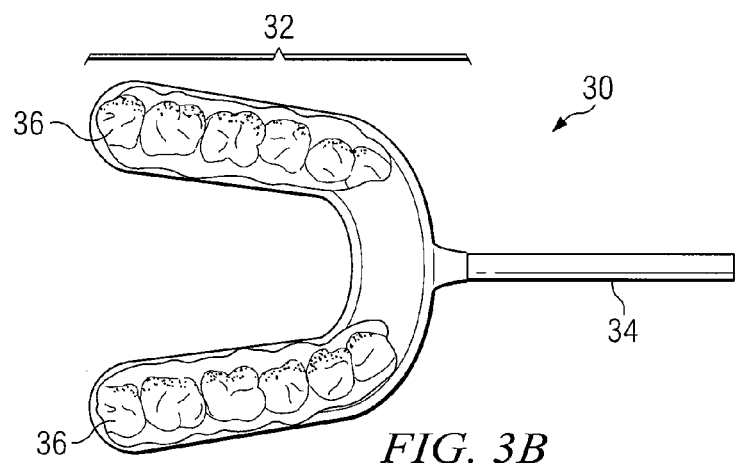
Figure 3C:
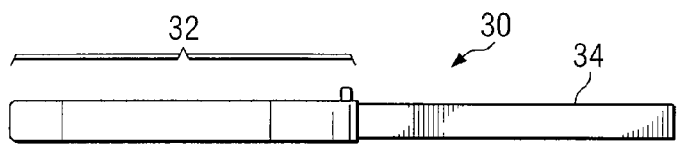
Figure 3D:
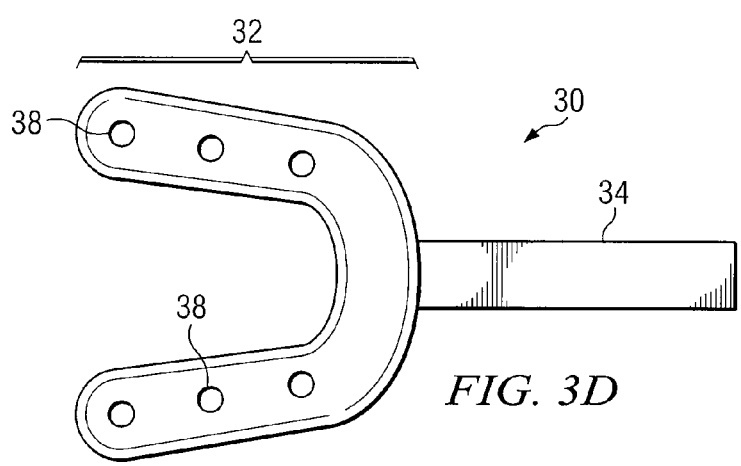

In certain embodiments, as shown in FIGS. 3C and 3D, bite plate 32 may include one or more features to aid in positioning and retaining deformable material 36 on bite plate 32. For example, bite plate 32 may include a plurality of holes recesses, and/or protrusions 38.

Post 34 represents a structure configured to project out of the user's mouth when the user bites down on bite plate 32. Post 34 provides a structure that may allow the user or a clinician to position bite plate 32 within the user's mouth and to remove bite plate 32 from the user's mouth. In addition, the relative position of post 34 to the user's teeth while the user is biting down on bite plate 32 is recorded by the impressions of the user's teeth in deformable material 36, which has a fixed position relative to post 34. In certain embodiments, post 34 may be substantially straight and have a circular cross-section, as shown in FIGS. 3A and 3B. As one alternative, post 34 may be substantially straight and have a rectangular cross-section, as shown in FIGS. 3C and 3D. Post 34 may have any appropriate shape and any appropriate cross-section according to particular needs.

Figure 4A:
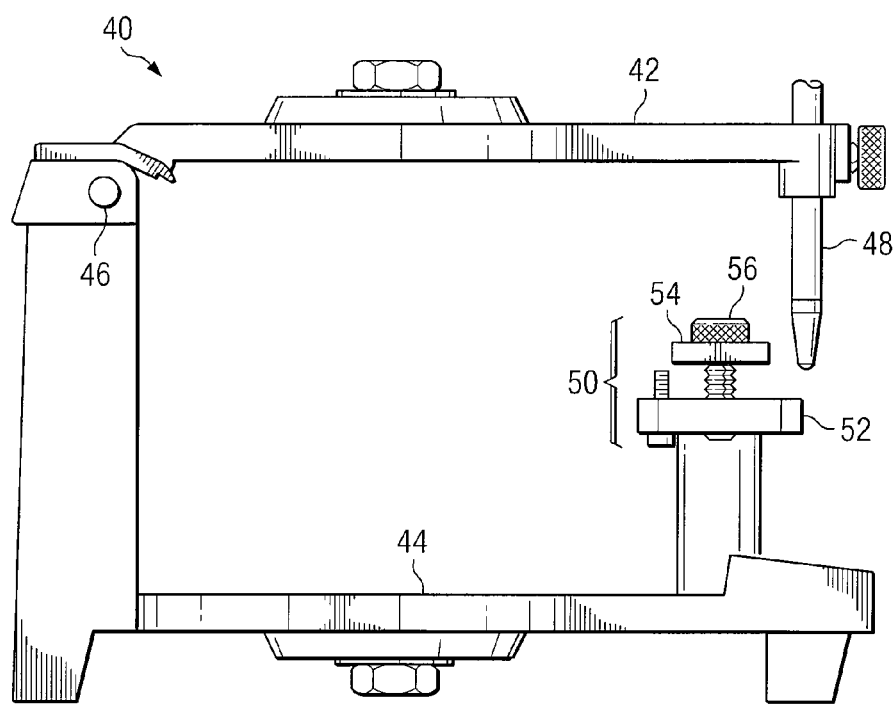
FIGS. 4A and 4B illustrate an example fixture for use in forming a custom oral appliance.
Figure 4B:
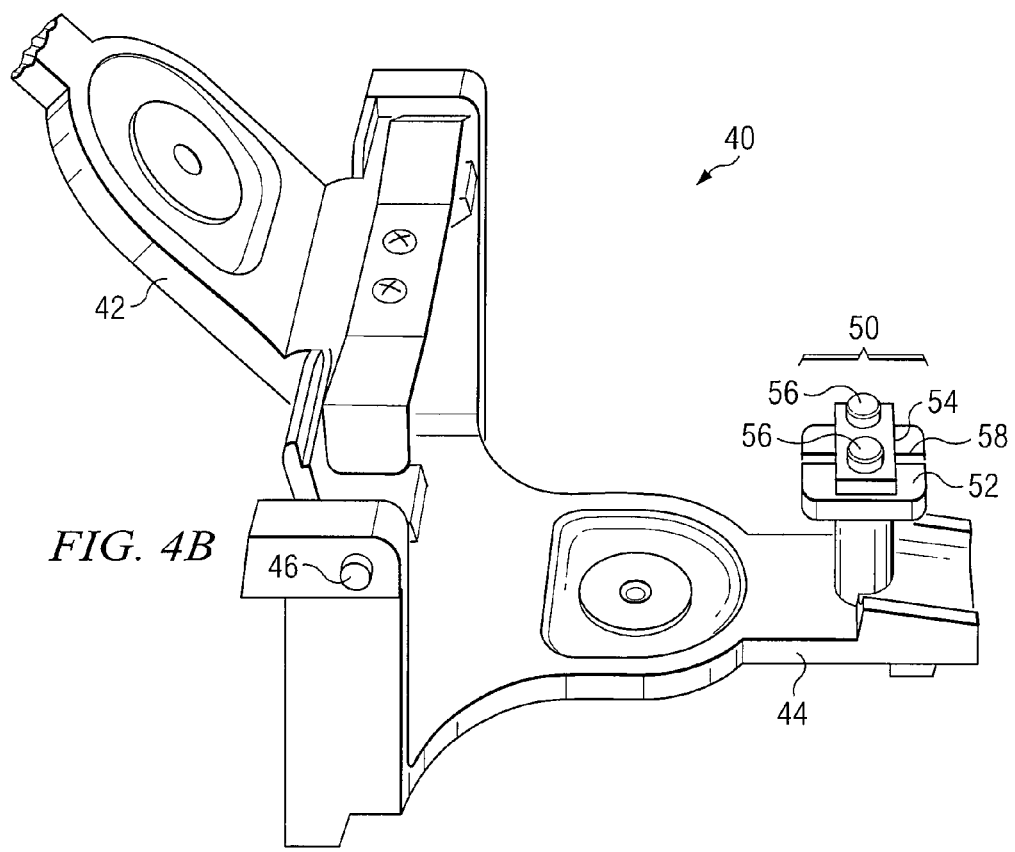

FIGS. 4A and 4B illustrate an example fixture 40 for use in forming custom oral appliance 10. Fixture 40 represents a device used to position one or more dental models during the forming of custom oral appliance 10. In certain embodiments, fixture 40 may represent a dental articulator used to replicate the movement of a person's jaw. In certain embodiments, fixture 40 includes an upper plate 42, lower plate 44, hinge 46, clamp 50, and adjustable stop 48. In alternate embodiments, fixture 40 may only include a single plate and clamp 50. In a particular embodiment, fixture 40 may be formed by adding clamp 50 to a DENTRONICS ARTICULATOR, available from GLIDEWELL LABORATORIES of Newport Beach, Calif.

Clamp 50 represents a device for positioning and securing one or more structures in fixture 40. In certain embodiments, clamp 50 includes one or more structures configured to repeatedly position and secure a post, such as post 16 of custom oral appliance 10 or post 34 of bite register 30. In certain embodiments, clamp 50 may include lower member 52, upper member 54, and adjustment member 56. In certain embodiments, clamp 50 may also include channel 58 to assist in repeatably positioning post 16 or post 34 within clamp 50. For example, channel 58 may allow post 16 or post 34 to be repeatably positioned such that the orientation of post 16 or post 34 relative to fixture 40 is substantially the same each time such a post is positioned. Channel 58 may align the long axis of post 16 or post 34 relative to fixture 40 to establish a defined orientation of post 16 or post 34. In certain embodiments, clamp 50 may allow post 16 or post 34 to rotate about, or translate along, the long axis of post 16 or post 34 without the orientation of post 16 or post 34 being changed.

FIGS. 5A through 5E illustrate an example method for forming custom oral appliance 10 using upper dental model 20 and lower dental model 22. Although in certain embodiments, as shown in FIGS. 5A through 5E and described below, custom oral appliance 10 may include both upper arch 12 and lower arch 14 and may be formed using both upper dental model 20 and lower dental model 22, in alternative embodiments custom oral appliance 10 may include a single arch 12 or 14 and be formed using a single dental model 20 or 22.

Figure 5A:
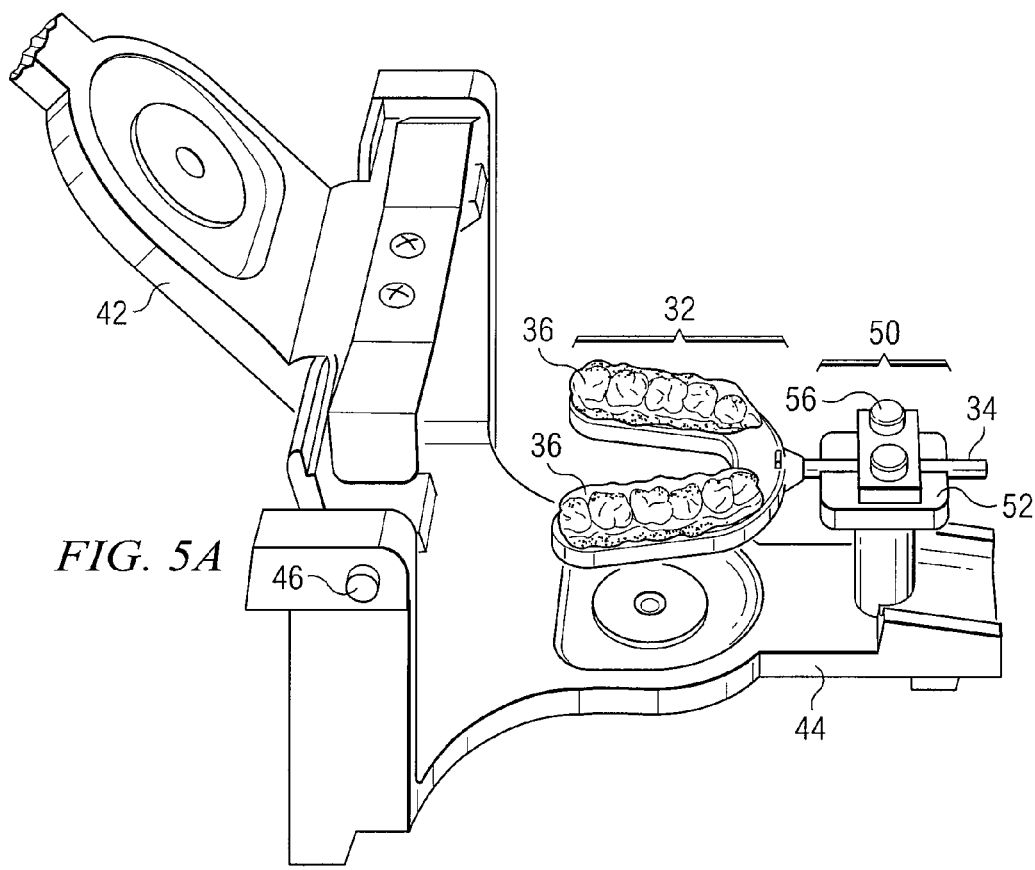

As shown in FIG. 5A, once an impression of a particular user's teeth has been made using bite register 30, bite register 30 is positioned within and secured using clamp 50. In certain embodiments, one or more features of bite register 30 and/or clamp 50 may be utilized to precisely position post 34 of bite register 30 within clamp 50. For example, clamp 50 may include channel 58 to precisely position post 34 of bite register 30 within clamp 50 to establish a defined orientation of post 34 relative to fixture 40.

Figure 5B:
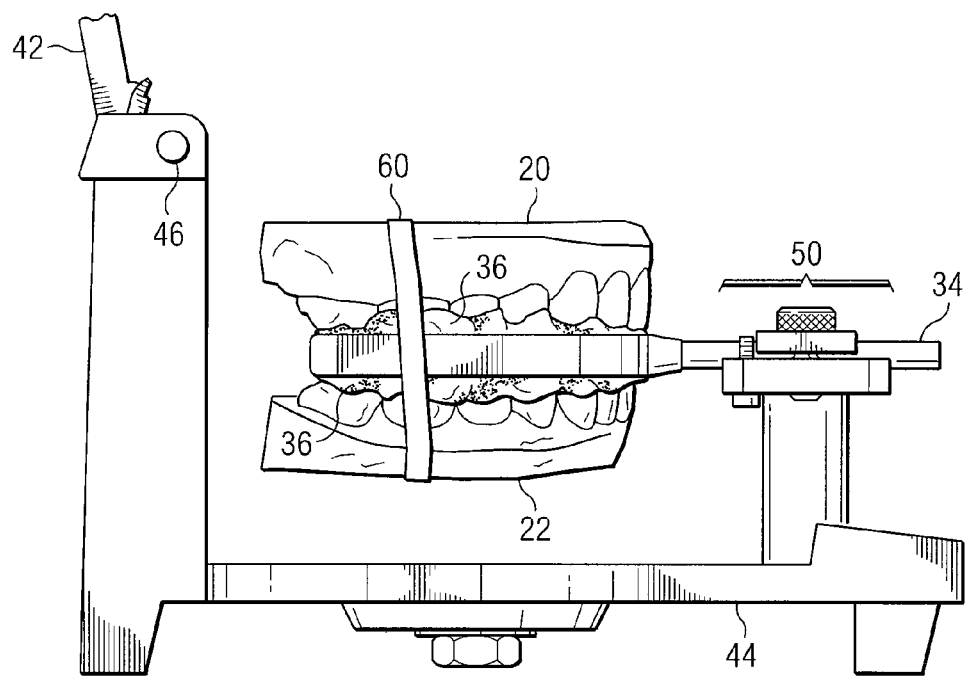

As shown in FIG. 5B, dental models 20 and 22 are seated within deformable material 36 of bite register 30. In certain embodiments, one or more devices may be used to hold dental models 20 and 22 together with bite register 30. For example, one or more elastic bands 60 may be utilized to hold dental models 20 and 22 together with bite register 30.

Figure 5C:
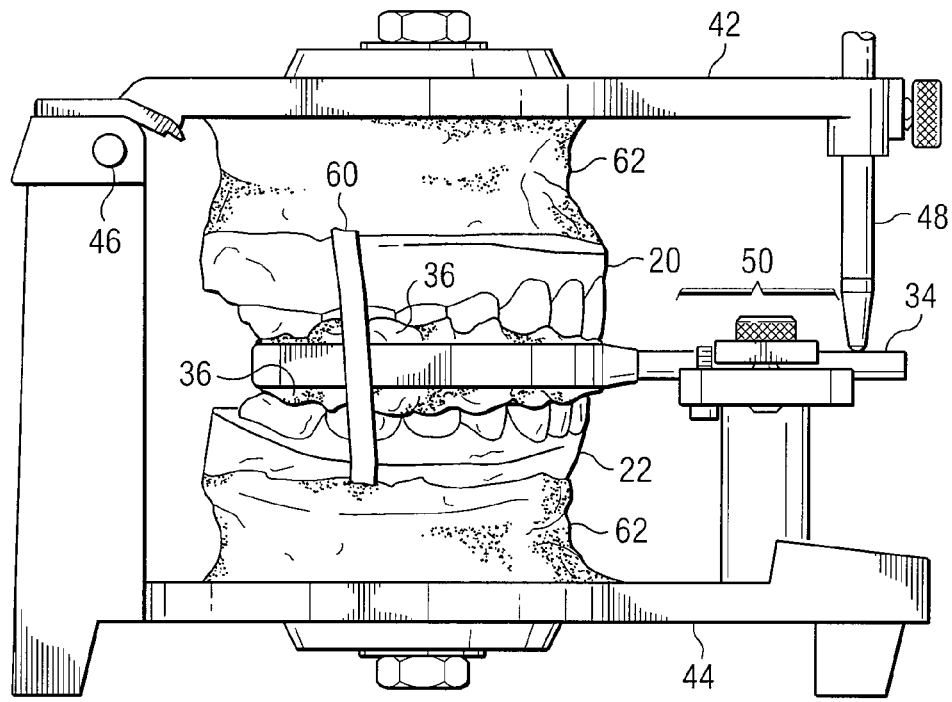

As shown in FIG. 5C, dental models 20 and 22 are coupled to plates 42 and 44, respectively, of fixture 40. In certain embodiments, dental models 20 and 22 may be coupled to plates 42 and 44 using plaster, stone, polymer, or any other appropriate material. For example, dental models 20 and 22 may be coupled to plates 42 and 44 by filling the gaps between dental models 20 and 22 and plates 42 and 44 with a dental plaster or a dental stone 62. In alternative embodiments, dental models 20 and 22 may be coupled to plates 42 and 44 using one or more clamps or other appropriate devices.

Figure 5D:
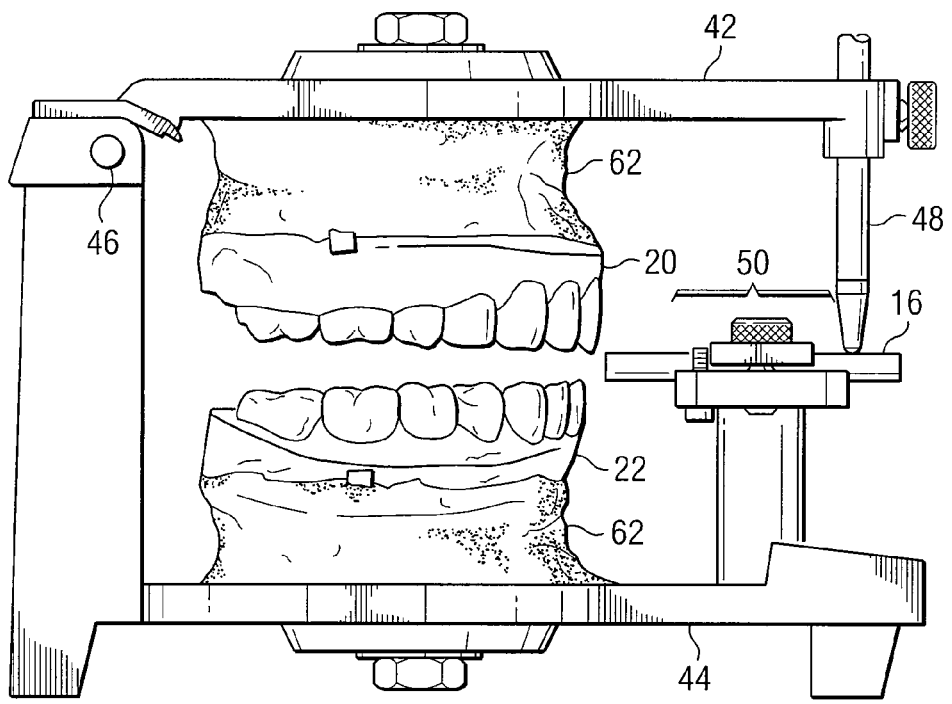

As shown in FIG. 5D, after dental models 20 and 22 have been coupled to plates 42 and 44, respectively, bite register 30 is removed from clamp 50. Post 16 is then positioned within and secured using clamp 50. In certain embodiments, post 16 is positioned within clamp 50 such that post 16 has substantially the same orientation relative to fixture 40 as post 34 had relative to fixture 40.

As shown in FIG. 5E, while dental models 20 and 22 are coupled to plates 42 and 44, respectively, and while post 16 is positioned within and secured using clamp 50, custom oral appliance 10 may be formed. In certain embodiments, upper arch 12 and lower arch 14 may be custom-formed to receive at least some of the particular user's teeth. Upper arch 12 and lower arch 14 may be custom-formed using dental models 20 and 22. In certain embodiments, this custom-forming may be performed while dental models 20 and 22 are coupled to plates 42 and 44. In alternative embodiments, this custom-forming may be performed before dental models 20 and 22 have been coupled to plates 42 and 44.

In certain embodiments, upper arch 12 and lower arch 14 may be custom-formed by applying a deformable material to upper dental model 20 and lower dental model 22, respectively. In one embodiment, the deformable material is heated to approximately 150° F. or other appropriate temperature suitable to place the deformable material in its deformable state. The deformable material is applied to dental models 20 and 22, such that deformable material conforms to the shape of at least some of the teeth of dental models 20 and 22. Deformable material is allowed to cool and harden to form a mold of the at least some of the teeth of dental models 20 and 22.

In certain embodiments utilizing connector 18, connector 18 may be positioned adjacent one or both of upper dental model 20 and lower dental model 22, such that when the deformable material is applied to upper dental model 20 and/or lower dental model 22, the deformable material conforms to at least a portion of connector 18 to couple connector 18 to one or both of upper arch 12 and lower arch 14. In alternative embodiments utilizing connector 18, connector 18 may be coupled to custom oral appliance 10 after the deformable material is allowed to cool and harden. In these embodiments, connector 18 may be coupled to custom oral appliance 10 using, for example, a further application of the deformable material, an appropriate adhesive, or one or more screws or other appropriate fasteners.

While dental models 20 and 22 are coupled to plates 42 and 44, respectively, and received within upper arch 12 and lower arch 14, respectively, post 16 is coupled to one or more of upper arch 12, lower arch 14, and connector 18 to form custom appliance 10. In embodiments in which post 16 is coupled to connector 18, connector 18 may include an opening to receive post 16 and post 16 may be secured using one or more set-screws, an appropriate adhesive, or other appropriate technique. In certain embodiments, post 16 may be coupled to one or more of upper arch 12, lower arch 14, and connector 18 through the application of a deformable material, such that when the deformable material hardens post 16 is rigidly coupled to custom oral appliance 10. In certain embodiments, post 16 is coupled to custom oral appliance 10 such that after post 16 is released from clamp 50, post 16 maintains the same orientation relative to fixture 40 as post 34 had to fixture 40.

In certain embodiments, using the methods described with respect to FIGS. 5A-5E, custom oral appliance 10 may be formed with a precisely located post 16 having substantially the same orientation relative to the particular user's teeth when the user wears custom oral appliance 10 as post 34 of bite register 30 had to the particular user's teeth when bite register 30 was used to form an impression of the user's teeth. In certain embodiments, using these methods, custom oral appliance 10 may be formed in an efficient manner, without the need for multiple office visits by the user. For example, in a single office visit, a clinician may obtain impressions of the user's teeth for use in forming dental models 20 and 22, and also obtain impressions of the user's teeth in bite register 30. Similarly, in the same office visit, a clinician may record the precise orientation of post 34 of bite register 30 relative to one or more unique features of the user's face. For example, the precise orientation of post 34 may be recorded by applying an impression material over the user's face and mouth while the bite register 30 is in the user's mouth, with post 34 projecting out of the user's mouth. As another example, the precise orientation of post 34 may be recorded by scanning the user's face and mouth with an electronic scanning device while the bite register 30 is in the user's mouth, with post 34 projecting out of the user's mouth. Using either a physical impression or an electronic impression of the user's face, a device such as a clinical gas delivery device may be formed that is custom-fitted to the user's face and is custom-fitted to couple to post 34 and post 16. Thus, following a single office visit by the user, a clinician or third-party may form custom oral appliance 10 and one or more devices configured to precisely couple to custom oral appliance 10.

Although example embodiments are described with reference to FIGS. 5A-5E, certain of the illustrated steps may be performed differently or in a different order without departing from the scope of the invention. For example, in certain embodiments, dental models 20 and 22 may be seated within bite register 30 before bite register 30 is coupled to fixture 40. As another example, in certain embodiments, post 34 may be removable from bite register 30 and subsequently post 34 may be used as post 16 of custom oral appliance 10. As another example, in certain embodiments, lower dental model 22 may be seated in bite register 30 and coupled to fixture 40 before upper dental model 20 is seated in bite register 30. As another example, in certain embodiments, only a single dental model 20 or 22 may be used to form a custom oral appliance 10 with a single arch 12 or 14. The present invention contemplates methods with additional steps, fewer steps, or different steps.

FIG. 6 illustrates an example mask 70 for use with an example custom oral appliance 10. Mask 70 represents an example clinical gas delivery device for coupling to post 16 of custom oral appliance 10. Mask 70 includes body 72, fitting 74, coupler 76, and set-screw 78. Body 72 provides a substantially air-tight seal against portions of the particular user's face. Fitting 74 is configured to couple to a clinical gas delivery system, such as a CPAP or BiPAP system, to deliver a clinical gas to the user. Coupler 76 is configured to receive post 16 to precisely couple custom oral appliance 10 to mask 70. Set-screw 78 represents an example structure for securing post 16 within coupler 76.

In certain embodiments, mask 70 or another device for use with custom oral appliance 10 may be custom-formed to precisely couple with post 16 of custom oral appliance 10. For example, mask 70 may be custom-formed to fit the user's unique facial features and to precisely couple to post 16 of custom oral appliance 10 based on an impression of the user's face, and of post 34 of bite register 30, taken while bite plate 32 was positioned between the user's upper and lower teeth.

Figure 7:
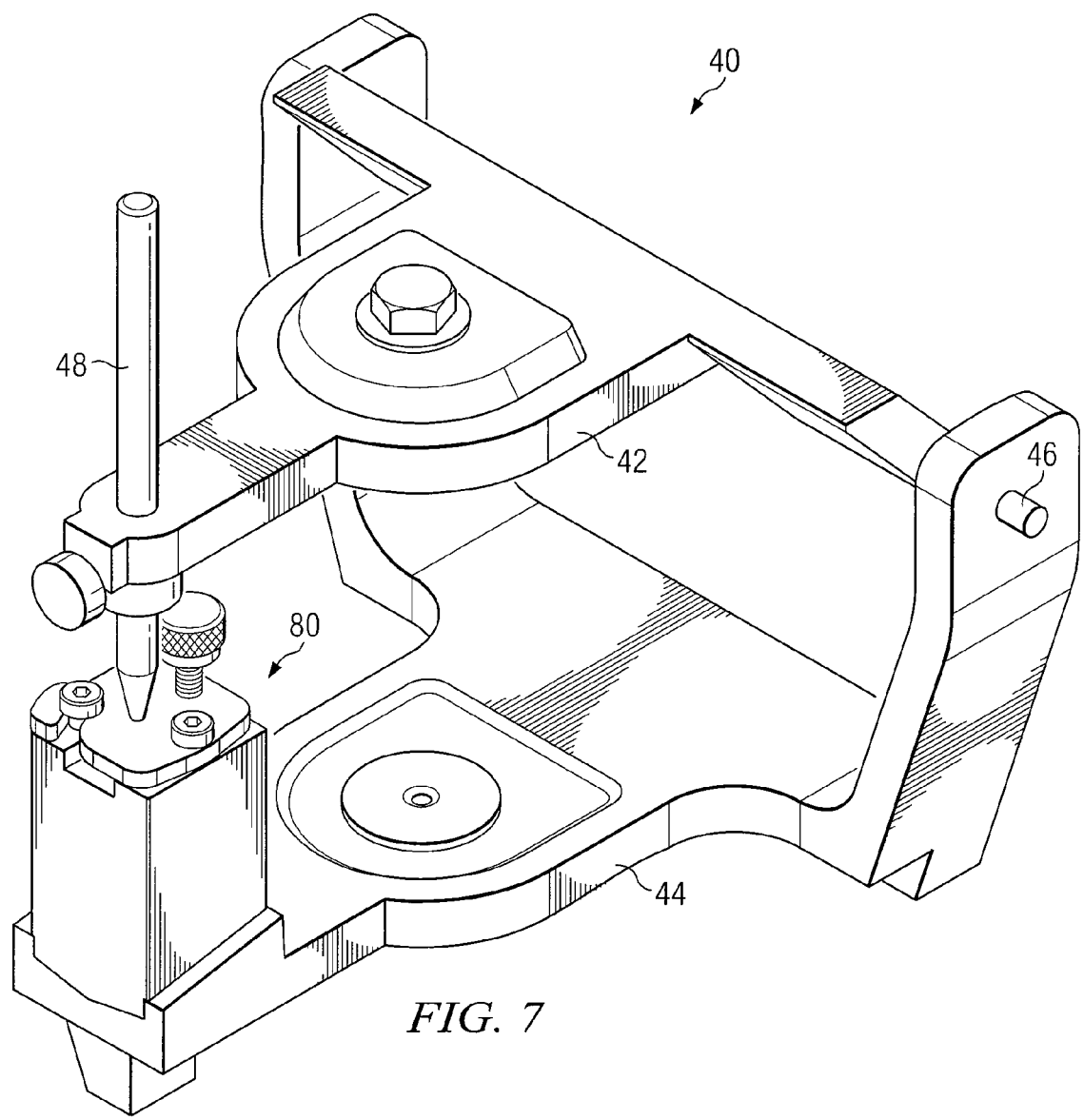
FIG. 7 illustrates an example fixture for use in forming a custom oral appliance.

FIG. 7 illustrates another example fixture 40 for use in forming custom oral appliance 10. In the embodiment shown, fixture 40 includes upper plate 42, lower plate 44, hinge 46, clamp 80, and adjustable stop 48. Clamp 80 represents a device for positioning and securing one or more structures in fixture 40. In certain embodiments, clamp 80 includes one or more structures configured to repeatably position and secure a post, such as post 16 of custom oral appliance 10 or post 34 of bite register 30.

Figure 8:
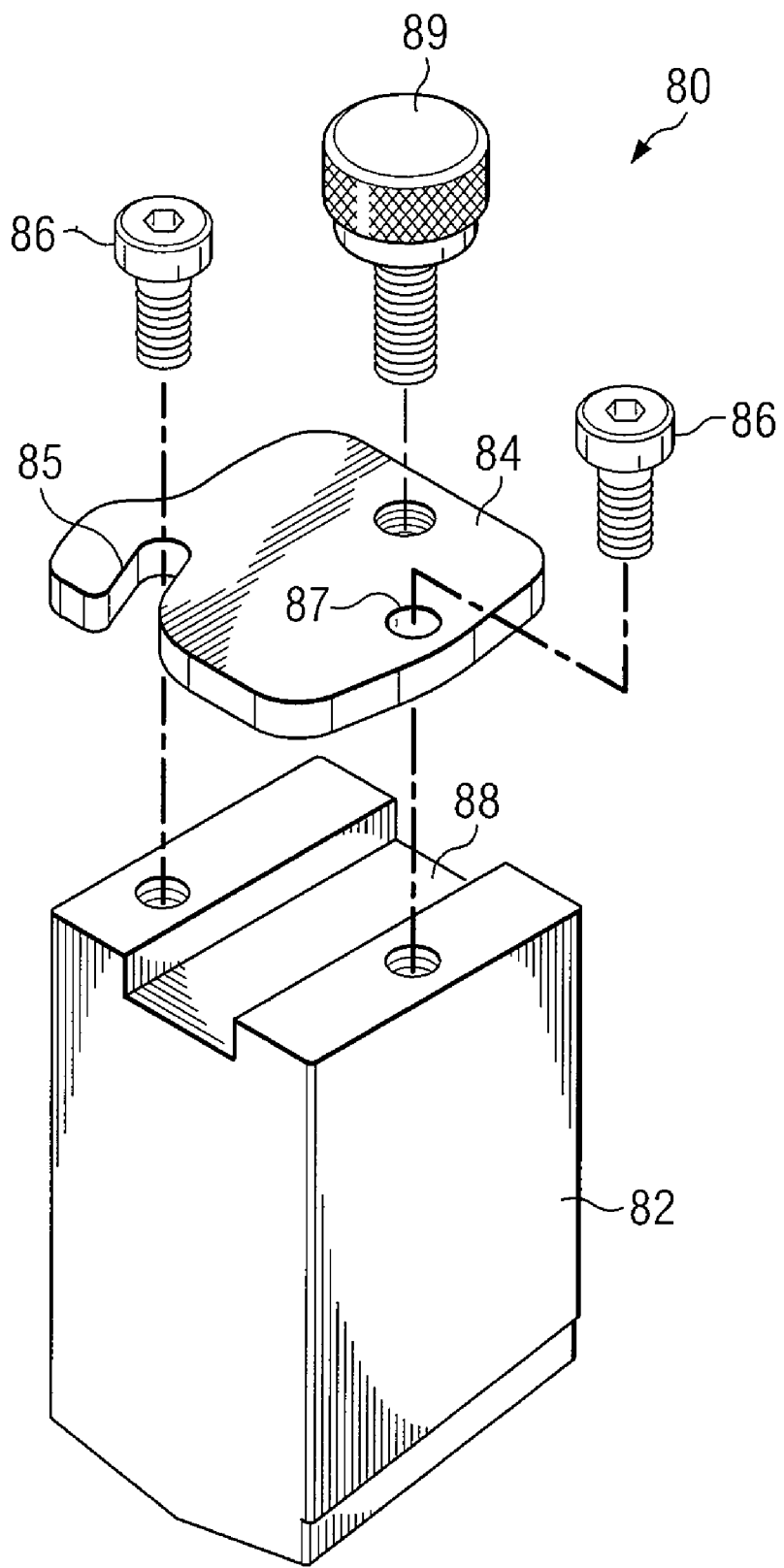
FIG. 8 illustrates an example clamp for use with an example fixture.

FIG. 8 illustrates an exploded view of an example clamp 80, according to a particular embodiment. In the embodiment shown, clamp 80 includes lower member 82, upper member 84, couplers 86, and adjustor 89. Upper member 82, lower member 84, couplers 86, and adjustor 89 may be formed from any appropriate material, including, for example, any appropriate metals, alloys, ceramics, or polymers. In certain embodiments, clamp 80 may include channel 88 to assist in retaining and repeatably positioning post 16 or post 34 within clamp 80. For example, channel 88 may allow post 16 or post 34 to be repeatably positioned such that the orientation of post 16 or post 34 relative to fixture 40 is substantially the same each time such a post is positioned. Channel 88 may align the axis of post 16 or post 34 relative to fixture 40 to establish a defined orientation of post 16 or post 34. In certain embodiments, clamp 80 may allow post 16 or post 34 to translate along the long axis of post 16 or post 34 without changing the orientation of post 16 or post 34.

Lower member 82 may couple to base plate 44 of fixture 40. In certain embodiments, the location of lower member 82 relative to base plate 42 may be fixed or adjustable. For example, in certain embodiments, lower member 82 may be linearly adjustable along a path substantially perpendicular to the axis of hinge 46. In certain embodiments, lower member 82 may include one or more portions configured to define one or more openings 83 to receive one or more couplers 86. The one or more openings 83 may or may not be threaded.

Upper member 84 may be configured to couple to lower member 82 to position and/or retain post 16 or post 34 within clamp 80. In certain embodiments, upper member 84 may be a plate configured to receive at least one coupler 86 and at least one adjustor 89. In a particular embodiment, upper member 84 includes a portion or portions configured to define one or more slots 85, and a portion or portions configured to define one or more openings 87. The one or more openings 87 may or may not be threaded.

Coupler 86 may be configured to position and/or retain upper member 84 relative to lower member 82. Although coupler 86 may be any appropriate device for positioning and/or retaining upper member 84, in certain embodiments, coupler 86 may be a post, screw, pin, or rivet. In certain embodiments, a first coupler 86 may function as a hinge or pivot for upper member 84 and a second coupler 86 may function as a stop to locate upper member 84 about an axis defined by first coupler 86. In a particular embodiment, clamp 80 may include two couplers 86 and the couplers 86 may be threaded hex-head machine screws that can inserted into threaded openings 83 in lower member 82.

Adjustor 89 may be configured to adjust upper member 84 relative to lower member 82, to lock or restrain upper member 84 relative lower member 84, and/or to restrain a post inserted into clamp 80. Although adjustor 89 may represent any appropriate device, in certain embodiments adjustor 89 may be a set screw or thumb screw. In particular embodiments, adjustor 89 may be a threaded knurled-head machine screw that can be inserted into a threaded opening 90 in upper member 84. In certain embodiments, adjustor 89 may be positioned over channel 88 when upper member 84 is located using couplers 86.

In operation, according to a particular embodiment, bite register 30 may be utilized to obtain dental impressions of a user's upper and lower dentitions. Post 34 of bite register 30 may be placed in channel 88 of clamp 80. Upper member 84 may be rotated about a first coupler 86 until slot 85 engages a second coupler 86. Couplers 86 may be tightened to secure upper member 84 relative to lower member 82. Post 34 may be linearly adjusted along channel 88, until a desired location is obtained, and adjustor 89 may be tightened to secure post 34 within clamp 80 at the desired location. Although this particular embodiment has been described with particular steps being performed in a particular order, in alternative embodiments steps may be performed in a different order, and more, fewer, or different steps may be used. For example, in certain embodiments, the location of post 34 within channel 88 may be adjusted before upper member 84 is positioned relative to lower member 82. As another example, in certain embodiments, upper member 82 may be positioned relative to lower member 84 before post 34 is placed in channel 88 of clamp 80.

To assist in describing the features and interactions of certain components, relational terms have been used. For example, certain components have been described as being upper or lower components. It should be understood that these terms have been used to describe example implementations and are not intended to limit the scope of the claimed invention. To the contrary, in alternative embodiments, the spatial location of one or more of the components described may be reversed or altered. For example, in a particular embodiment, clamp 80 may be coupled to upper plate 42 rather than lower plate 44. Accordingly, in certain configurations, lower member 82 could be positioned above upper member 84 without departing from the scope of certain embodiments of the present invention.

Although the present invention has been described in several embodiments, a plenitude of changes, substitutions, variations, transformations, and modifications may be suggested to one skilled in the art, and it is intended that the present invention encompass such changes, substitutions, variations, transformations, and modifications as fall within the scope of the appended claims.

What is claimed is:

1. A method for forming a custom oral appliance, comprising:
   accessing a bite register for a particular user, the bite register comprising a bite register post, an upper impression of at least some of the particular user's upper teeth, and a lower impression of at least some of the particular user's lower teeth, wherein the upper impression and the lower impression are coupled to the bite register post;
   accessing an upper dental model of at least some of the particular user's upper teeth and a lower dental model of at least some of the particular user's lower teeth;
   accessing a fixture comprising an upper plate, a lower plate, and a clamp and configured to repeatably position and secure a post;

coupling the bite register post to the fixture using the clamp of the fixture, such that the bite register post has a first orientation relative to the fixture;

coupling the upper dental model and the lower dental model to the bite register, such that the upper dental model seats within the upper impression of the bite register and the lower dental model seats within the lower impression of the bite register;

while the upper dental model is seated within the upper impression of the bite register and the bite register post is coupled to the fixture, coupling the upper dental model to the upper plate of the fixture;

while the lower dental model is seated within the lower impression of the bite register and the bite register post is coupled to the fixture, coupling the lower dental model to the lower plate of the fixture;

while the upper dental model is coupled to the upper plate of the fixture and the lower dental model is coupled to the lower plate of the fixture, uncoupling the bite register from the upper dental model, the lower dental model, and the fixture;

coupling an oral appliance post to the fixture using the clamp of the fixture, such that the oral appliance post has a second orientation relative to the fixture, the second orientation of the oral appliance post being the same as the first orientation of the bite register post;

while the upper dental model, the lower dental model, and the oral appliance post are coupled to the fixture, forming a custom oral appliance that is custom-fitted to the upper dental model and the lower dental model, such that the custom oral appliance couples to the oral appliance post and maintains the second orientation of the oral appliance post.

2. The method of claim 1, wherein:
the fixture clamp comprises a groove;
coupling the bite register post to the fixture comprises aligning the bite register post with the groove of the fixture clamp; and
coupling the oral appliance post to the fixture comprises aligning the oral appliance post with the groove of the fixture clamp.

3. The method of claim 1, wherein coupling the dental models to the fixture plates comprises filling gaps between the dental models and the fixture plates with a dental plaster or a dental stone.

4. The method of claim 1, wherein forming the custom oral appliance comprises:
placing a deformable material in a deformable state;
applying the deformable material to the dental models; and
allowing the deformable material to harden.

5. The method of claim 4, wherein the deformable material comprises a polycaprolactone polymer.

6. The method of claim 1, wherein the custom oral appliance comprises an upper arch custom-fitted to the upper dental model and configured to receive at least some of the particular user's upper teeth, a lower arch custom-fitted to the lower dental model and configured to receive at least some of the particular user's lower teeth, and a connector configured to couple the upper arch to the lower arch.

7. The method of claim 1, wherein the connector is configured to adjust the forward position of the lower arch relative to the upper arch.

8. The method of claim 1, wherein the fixture comprises a dental articulator.

9. A method for forming a custom oral appliance, comprising:

accessing a bite register for a particular user, the bite register comprising a bite register post, an upper impression of at least some of the particular user's upper teeth, and a lower impression of at least some of the particular user's lower teeth, wherein the upper impression and the lower impression are coupled to the bite register post;

accessing an upper dental model of at least some of the particular user's upper teeth and a lower dental model of at least some of the particular user's lower teeth;

accessing an upper arch custom-fitted to the upper dental model and configured to receive at least some of the particular user's upper teeth, a lower arch custom-fitted to the lower dental model and configured to receive at least some of the particular user's lower teeth, and a connector that couples the upper arch to the lower arch;

accessing a fixture comprising an upper plate, a lower plate, and a clamp and configured to repeatably position and secure a post;

coupling the bite register post to the fixture using the clamp of the fixture, such that the bite register post has a first orientation relative to the fixture;

coupling the upper dental model and the lower dental model to the bite register, such that the upper dental model seats within the upper impression of the bite register and the lower dental model seats within the lower impression of the bite register;

while the upper dental model is seated within the upper impression of the bite register and the bite register post is coupled to the fixture, coupling the upper dental model to the upper plate of the fixture;

while the lower dental model is seated within the lower impression of the bite register and the bite register post is coupled to the fixture, coupling the lower dental model to the lower plate of the fixture;

while the upper dental model is coupled to the upper plate of the fixture and the lower dental model is coupled to the lower plate of the fixture, uncoupling the bite register from the upper dental model, the lower dental model, and the fixture;

coupling an oral appliance post to the fixture using the clamp of the fixture, such that the oral appliance post has a second orientation relative to the fixture, the second orientation of the oral appliance post being the same as the first orientation of the bite register post;

positioning the upper arch relative to the upper dental model such that at least some of the teeth of the upper dental model seat within the upper arch;

positioning the lower arch relative to the lower dental model such that at least some of the teeth of the lower dental model seat within the lower arch; and while the upper dental model, the lower dental model, and the oral appliance post are coupled to the fixture, and while at least some of the teeth of the upper dental model are received within the upper arch and at least some of the teeth of the lower dental model are received within the lower arch, coupling the oral appliance post to the connector coupling the upper arch to the lower arch to form a custom oral appliance that is custom-fitted to the upper dental model and the lower dental model and maintains the second orientation of the oral appliance post.

10. The method of claim 9, wherein:
the fixture clamp comprises a groove;
coupling the bite register post to the fixture comprises aligning the bite register post with the groove of the fixture clamp; and coupling the oral appliance post to the fixture comprises aligning the oral appliance post with the groove of the fixture clamp.

11. The method of claim 9, wherein coupling the dental models to the fixture plates comprises filling gaps between the dental models and the fixture plates with a dental plaster or a dental stone.

12. The method of claim 9, wherein the upper arch and the lower arch comprise a polycaprolactone polymer.

13. The method of claim 9, wherein the connector is adjustable and is configured to adjust the forward position of the lower arch relative to the upper arch.

14. The method of claim 9, wherein the fixture comprises a dental articulator.

15. A method for forming a custom oral appliance, comprising:
- accessing a bite register for a particular user, the bite register comprising an impression of at least some of the particular user's teeth and a bite register post, wherein the impression is coupled to the bite register post;
- accessing a dental model of at least some of the particular user's teeth;
- accessing a fixture comprising a plate and a clamp and configured to repeatably position and secure a post;
- coupling the bite register post to the fixture using the clamp of the fixture, such that the bite register post has a first orientation relative to the fixture;
- coupling the dental model to the bite register, such that the dental model seats within the impression of the bite register;
- while the dental model is seated within the impression of the bite register and the bite register post is coupled to the fixture, coupling the dental model to the plate of the fixture;
- while the dental model is coupled to the plate of the fixture, uncoupling the bite register from the dental model and the fixture;
- coupling an oral appliance post to the fixture using the clamp of the fixture, such that the oral appliance post has a second orientation relative to the fixture, the second orientation of the oral appliance post being the same as the first orientation of the bite register post; and
- while the dental model and the oral appliance post are coupled to the fixture, forming a custom oral appliance that is custom-fitted to the dental model, such that the custom oral appliance couples to the oral appliance post and maintains the second orientation of the oral appliance post.

16. The method of claim 15, wherein:
the fixture clamp comprises a groove;
coupling the bite register post to the fixture comprises aligning the bite register post with the groove of the fixture clamp; and
coupling the oral appliance post to the fixture comprises aligning the oral appliance post with the groove of the fixture clamp.

17. The method of claim 15, wherein coupling the dental model to the fixture plate comprises filling a gap between the dental model and the fixture plate with a dental plaster or a dental stone.

18. The method of claim 17, wherein forming the custom oral appliance comprises:
placing a deformable material in a deformable state;
applying the deformable material to the dental model; and
allowing the deformable material to harden.

19. The method of claim 15, wherein the deformable material comprises a polycaprolactone polymer.

20. The method of claim 15, wherein the custom oral appliance comprises an arch custom-fitted to the dental model and configured to receive at least some of the particular user's teeth.

21. The method of claim 15, wherein the fixture comprises a dental articulator.

* * * * *